United States Patent [19]

Ewald

[11] Patent Number: 5,038,806
[45] Date of Patent: Aug. 13, 1991

[54] DISPOSABLE DENTAL FLOSSER AND HOLDER

[76] Inventor: Howard H. Ewald, 2300 Patrick La., #15, Las Vegas, Nev. 89119

[21] Appl. No.: 602,039

[22] Filed: Oct. 19, 1990

Related U.S. Application Data

[63] Continuation-in-part of Ser. No. 269,104, Nov. 7, 1988, Pat. No. D. 311,595.

[51] Int. Cl.$^5$ .............................................. A61C 15/00
[52] U.S. Cl. ................................... 132/325; 132/324
[58] Field of Search ............... 132/322, 323, 324, 325, 132/326, 327

[56] References Cited

U.S. PATENT DOCUMENTS

| | | | |
|---|---|---|---|
| 2,735,436 | 2/1956 | Russo | 132/323 |
| 3,631,869 | 1/1972 | Espinosa | 132/323 |
| 3,871,392 | 3/1975 | Thomas | 132/323 |
| 3,924,647 | 12/1975 | Lindblad | 132/326 |
| 3,927,687 | 12/1975 | Thierman | 132/325 |
| 4,178,947 | 12/1979 | McCourry et al. | 132/324 |
| 4,245,658 | 1/1981 | Lecouturier | 132/322 |

Primary Examiner—Robert P. Swiatek
Assistant Examiner—Michael Lynch
Attorney, Agent, or Firm—Jessup, Beecher & Slehofer

[57] ABSTRACT

A flosser has an elongate configuration with a forked arm at one end and an enlarged opposite end for housing a spool of unused dental floss, and a take-up reel for storing the dental floss as it is used. The dental floss is strung from the spool, across the arm, and back to the reel. There is a free knob having a spindle which connects the reel so that the feed knob and reel rotate in unison to reel in the spent floss. There is a cylindrical crown projection at the housing end that mates with the feed knob and encases the spool of unused dental floss. The feed knob and crown projection have a clutch mechanism allowing the feed knob and take-up reel to rotate in only one direction and to frictionally engage and hold the floss at the spool end and to temporarily disengage the floss when the feed knob is rotated to allow a measured amount of fresh floss to unwind from the freely rotatable spool, while simultaneously reeling in a like amount of spent floss into the take-up reel. The clutch mechanism rotates in incremental steps to advance new floss across the forked arm. The clutch mechanism also prevents the take-up reel from unwinding when the feed knob is at its at-rest position. Additional guide posts and guideways on the frame also provide tautness to the strung dental floss to keep it sufficiently taut while the invention is being used to floss teeth.

5 Claims, 5 Drawing Sheets

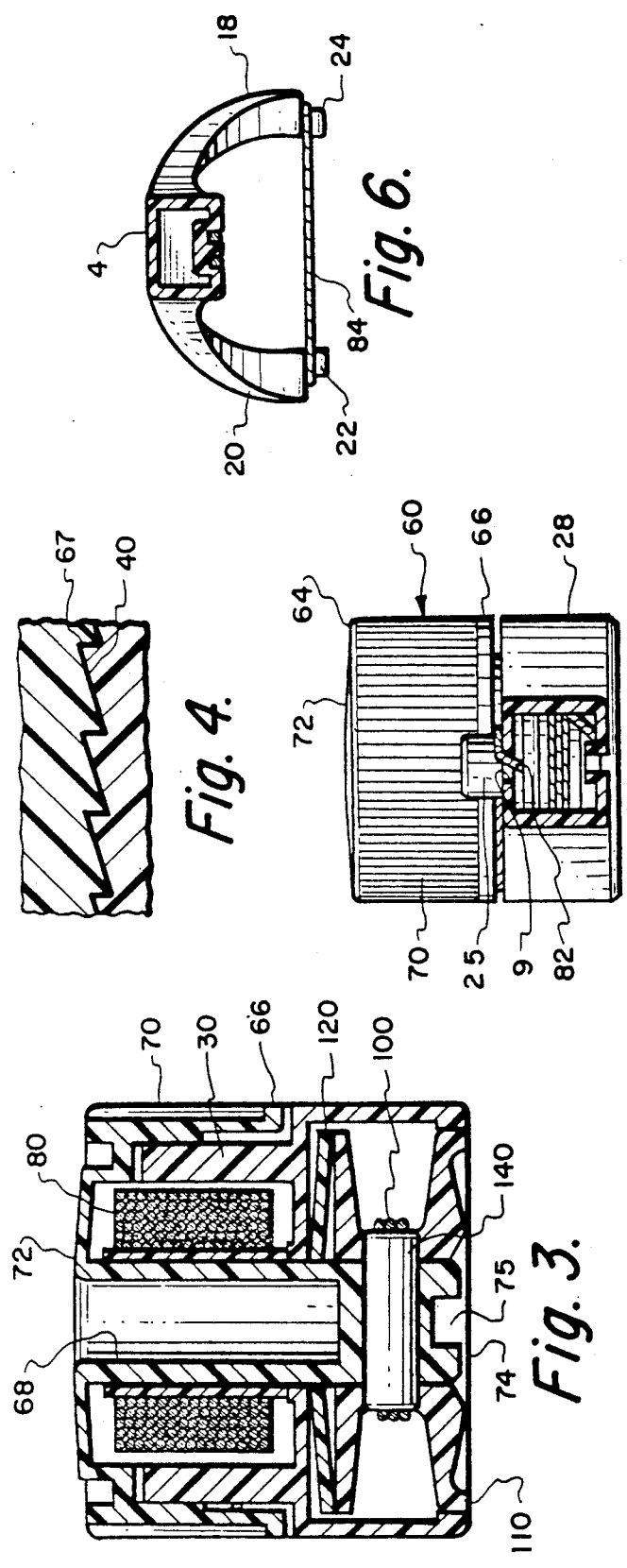
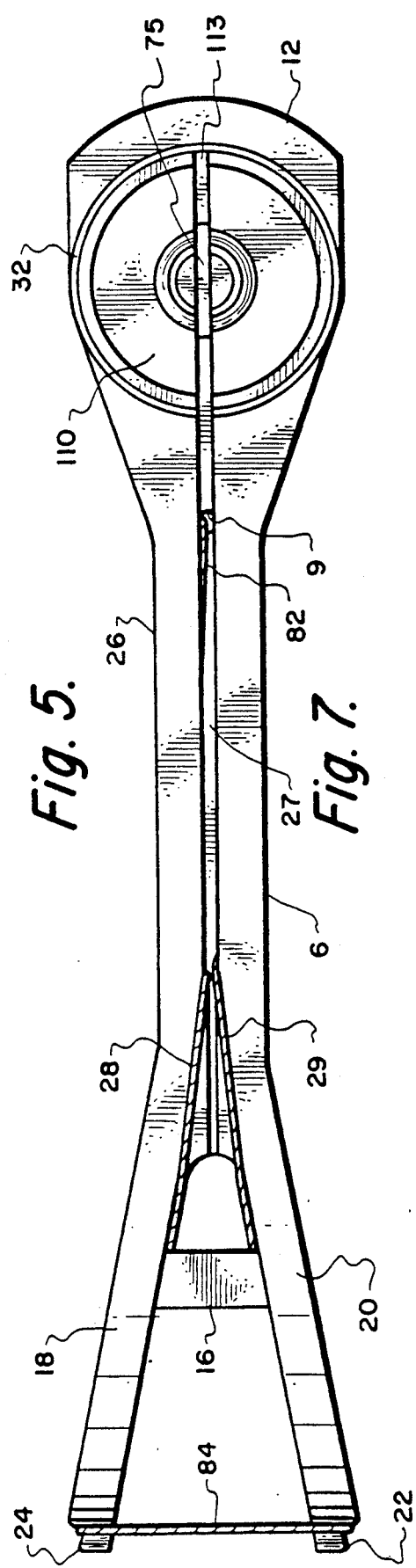

1

DISPOSABLE DENTAL FLOSSER AND HOLDER

CROSS REFERENCE TO RELATED APPLICATIONS

This is a Continuation-in-Part of application Ser. No. 07/269,104 filed on Nov. 7, 1988, now U.S. Pat. No. 0,311,595.

BACKGROUND OF THE INVENTION

1. Field of the Invention

Toilet toothpick; having thread holder, for example, flossing implement; and container or support for thread supply; including rotatably mounted thread spool.

2. Description of the Prior Art

Periodontal disease, or gum disease, is the major culprit in the loss of teeth among adults. Nearly half of all tooth loss by adults is the result of advanced periodontal disease. The chances of developing periodontal disease increases with age so that nearly all elderly people are affected to some degree by it. It is well established among dentists that the cause of periodontal disease is the buildup of plaque on the teeth. The best prevention against periodontal disease is to maintain good dental hygiene by regular brushing and flossing of one's teeth. Regular flossing is just as important as brushing. However, many adults no do not floss because of the inconvenience of having to tautly hold a piece of floss with the fingers while trying to perform the flossing task. Prethreaded flossers and floss holders are available for those people who have limited dexterity, or who prefer the convenience of a flosser or floss holder.

SUMMARY AND OPERATION OF THE INVENTION

The flosser has an elongate configuration with a forked arm at one end and an enlarged opposite end for housing a spool of unused dental floss, and a take-up reel for storing the dental floss as it is used. The dental floss is strung from the spool, across the arm, and back to the reel. There is a feed knob having a spindle which connects to the reel so that the feed knob and reel rotate in unison to reel in the spent floss. There is a cylindrical crown projection at the housing end that mates with the feed knob and encases the spool of unused dental floss. The feed knob and crown projection have a clutch mechanism allowing the feed knob and take-up reel to rotate in only one direction and to frictionally engage and hold the floss at the spool end and to temporarily disengage the floss when the feed knob is rotated to allow a measured amount of fresh floss to unwind from the freely rotatable spool, while simultaneously reeling in a like amount of spent floss onto the take-up reel. The clutch mechanism rotates in incremental steps to advance new floss across the forked arm. The clutch mechanism also prevents the take-up reel from unwinding when the feed knob is at its at-rest position. Additional guide posts and guideways on the frame also provide tautness to the strung dental floss to keep it sufficiently taut while the invention is being used to floss teeth.

Expressed another way, the present invention comprises six separate components, or pieces, which when assembled together form the disposable dental flosser and holder. The five components are: the frame; feed knob with spindle; take-up reel; spring washer; locking pin; and spool with a quantity of unused flossing thread.

In a preferred embodiment, the components other than the spool of dental floss, are fabricated by an injection molding process using high density polyethylene or polypropylene.

The frame is a hollow elongated component having a top, bottom, front and rear areas. There is a forked arm at the front end for stringing a portion of the dental floss. There is an enlarged open-ended compartment towards the back for housing both the unused floss and the spent floss. The midsection of the frame is narrowed down between the front and the back to form a neck for allowing the user to hold and manipulate the invention while the user is flossing his or her teeth. There is a longitudinal open gap running along the bottom of the frame and extending between the forked arm and the housing compartment.

The housing end of the frame has a cylindrical crown projection extending upwardly from the top surface of the frame. The top rim of the crown projection has a circular array of inclined teeth. The bottom cavity formed by the crown projection where it is attached to the frame has a small circular concentric opening that leads to the interior housing portion of the frame.

The bottom of the frame at the housing end contains a large circular opening concentric with the small circular opening in the top of the frame at the bottom of the crown projection.

The feed knob has a hollow cylindrical shape with a cap on the top and an axial spindle extending from the inside of the cap and beyond the bottom lip of the feed knob. There is a circular array of inclined teeth around the circular rim of the inside of the cap that is complementary to and mates with the circular array of inclined teeth at the top of the crown projection. The interior dimensions of the feed knob are slightly larger than the exterior dimensions of the crown projection so that the two elements can slip over and engage with one another. The spindle of the feed knob slips through the circular opening at the base of the crown projection and into the interior of the frame and extends to the bottom of the frame in the housing area. There is a transverse diametral bore positioned slightly inboard from the end of the feed knob spindle and there is a transverse diametral groove cut in the bottom tip of the spindle.

The take-up reel is formed like a fly fishing reel and has overall dimensions such that it can fit within the larger circular opening in the bottom of the frame and occupies that portion of the frame below the crown projection. The take-up reel also has an axial bore for mounting the reel towards the end of the spindle. The take-up reel also has a transverse diametral bore which has the same overall dimensions and is aligned with the diametral bore on the spindle. The locking pin is inserted into both bores thereby locking the take-up reel to the spindle and spatially positioning the take-up reel within the housing end of the frame. The feed knob and the take-up reel now rotate in unison, and both will rotate the same number of degrees per increment rotated by the feed knob. Before the take-up reel is locked on to the spindle, the belleville spring washer is slipped over the end of the spindle. The spring is placed on the spindle and between the top of the take-up reel and the flat inside face of the frame area concentric with the hole in the base of the crown projection. The space allowed for the spring washer is slightly less than its uncompressed thickness. The spring washer has the same size bore and overall diameter as the take-up reel. The spring washer has a slight hollow conical configuration so that it always exerts pressure between the inside top of the frame and the top circular face of the take-up reel. This tension keeps the matching pair of inclined ratchet teeth on the crown projection and inside of the feed knob cap together. The spring washer also functions to separate the spent floss on the take-up reel from the unused floss on the floss spool positioned on the other side of the frame.

The concentric bore drilled in the top of the frame and at the base of the cavity of the crown projection is just slightly larger than the diameter of the spindle to allow the spindle to pass through. This joint also tends to segregate the spent floss from the unused fresh floss. The spool of dental floss contains about 36 feet of new floss wound on the spool, or enough floss for over 600 flossings. The spool has an axial bore through which the spindle on the feed knob is passed as the components comprising the invention are assembled together. However, the spool holding the dental floss can rotate independently from the feed knob, because the diameter of the axial bore of the spool is much larger than the diameter of the spindle, which passes through the bore of the floss spool. The crown projection has a small opening drilled into its wall and directed towards the rear of the frame. Additionally this eyelet, or small hole, is approximately equidistant between the top and the bottom rims of the crown projection. Furthermore, the cylindrical inside surface of the feed knob has a pair of stepped cylindrical bores such that the lower bore is a slightly larger diameter than the upper bore. Additionally, the two cylindrical bore surfaces each are about the same width. The changing of the cylindrical surfaces causes a slight ledge to be formed on the inside surface of the feed knob.

When the invention is being assembled, the spool of new unused floss is initially threaded through the eyelet on the crown projection and there is a sufficient amount of string drawn through the eyelet in order to thread the floss on the frame and secure the end to the take-up reel. As previously stated, the feed knob has an axial shaft which extends into the body of the frame. The end of the shaft has the take-up reel secured to it by means of a locking pin. Interposed between the take-up reel and the inside top of the frame is a circular belleville washer. The belleville washer has a slight cone-shaped configuration. The height of the belleville washer is greater than the space between the take-up reel and the inside face of the frame causing the belleville washer always to be under tension when in place. This tension biases the lower rim or lip of the feed knob against the top outside surface of the frame. The portion of dental floss exiting from the lip has a drag placed on the floss because of the rim of the feed knob pressing against the exiting portion of the dental floss. This clamping action by the lip of the feed knob is effective to maintain the tautness of the dental floss strung between the forked arms while the invention is being used. After the components have been assembled to form the invention, the loose string of dental floss exiting from the lip of the feed knob is threaded along the guideway portions of the frame and back to the take-up reel in order to allow the feed knob's turning of the take-up reel to secure the loose end of the dental floss and to allow the take-up reel's rotation to take up the slack on the loose dental floss and to tighten it sufficiently so that the invention is ready to be used as a flosser.

In a preferred embodiment, there is a guide post positioned adjacent to the feed knob and in front of the feed knob on the top of the frame. Located adjacent to the guide post is a an eyelet opening to allow the loose end of the floss to be threaded through the eyelet, and it traverses along the interior of the frame until it is exposed again towards the forked arm. The purpose of the guide post also is to assist in the tensing of the dental floss in order to keep it sufficiently taut while in use, and to provide a means for the user to increase the floss tension by threading the floss with a complete turn around the guide post. The crimping action and friction on the floss exiting under the feed knob lip and around the guide post are sufficient to prevent the floss from easily unwinding from the spool caused by tension being placed against the strung dental floss while in use.

The spool of unused floss within the crown projection and feed knob is freely rotatable. It is not dependent on the rotation of the feed knob. Of course, it will rotate to let out unused floss as the take-up reel is being rotated, which is the normal usage in order to allow increments of unused dental floss to be drawn from the spool and across the forked arm where the dental floss is used.

The clutch mechanism formed by the complementary array of circular teeth on the crown projection and the inside cap of the feed knob and the spring loaded washer is intended to provide a means to traverse the floss along its track in a controlled fashion to allow new floss to be unwound from the dental flosser while the used floss is being taken up concurrently by the take-up reel and yet to prevent any slack from occurring along the track of the dental floss. The inclined array of complementary teeth allows the feed knob to rotate in one direction only; in this case clockwise. As the pair of inclined teeth rise up on each other in response to torque being placed on the feed knob by the user, the rotation will proceed increment by increment resulting in a "clicking" noise. During this clicking operation, the feed knob moves axially away from the body of the frame a small amount due to the mating inclined teeth rising up on each other. Thus the pressure on the floss under the lip of the feed knob is reduced and it is when the teeth jump over each other that the basic floss tension is established. When the manual rotation of the feed knob stops, the ratchet teeth completely mesh and full pressure returns under the feed knob lip so that the floss supply side is locked. The ratchet teeth completely mesh and full pressure returns under the feed knob lip so that the floss supply side is locked. The ratchet teeth do not allow the take-up reel to unwind. As a result, the basic tension of the exposed floss is maintained during flossing. Each incremental feed knob rotation results in a small portion of the floss being moved one increment along the floss track of the invention.

In normal operation, the user will rotate the feed knob several increments at a time while watching the new floss being strung across the forked arm until only new floss is in the strung position. Since the dental spool contains about 36 feet of unused floss, and about three-fourths of an inch increments of floss are unwound per use, one can expect that the user could use the invention over 500 times, or about one year.

Occasionally, because of an abrasion or the floss getting stuck between the teeth, the floss thread itself becomes broken. The present invention has a means to restring the floss around the frame to avoid having to dispose of the flosser invention before all of the fresh unused floss has been used up. The bottom of the take-up reel, which is exposed at the bottom of the frame, has a diametral slit and the bottom of the spindle likewise has a diametral groove. The two are cut such that when the take-up reel is mounted on the spindle by means of the locking pin, the groove on the spindle and the slit on the take-up reel are aligned.

To restring the cut floss, one merely has to align the slit on the reel along with the bottom slit previously formed in the bottom of the frame. One can thread the loose end of the floss through the slit on the reel and out through the open end of the housing area of the frame. While holding the loose end, one rotates the feed knob sufficiently so that a portion of the floss string winds on to the take up reel to secure it to the take-up reel and thereby maintaining the tension on the floss as it was before.

BRIEF DESCRIPTION OF THE DRAWINGS

FIG. 3 is a transverse sectional view taken along the line 3—3 of FIG. 2.

FIG. 4 is a fragmentary sectional view taken along the line 4—4 of FIG. 2.

FIG. 5 is a partial sectional view taken along the line 5—5 of FIG. 2.

FIG. 6 is a cross sectional view taken along the line 6—6 of FIG. 2.

FIG. 7 is a bottom plan view of the dental floss invention viewed from the line 7—7 of FIG. 2.

FIG. 14b is a sectional view of the take-up reel taken along the line 14b—14b of FIG. 14a.

FIG. 15b a sectional view of the feed knob taken along the line 15b—15b of FIG. 15a.

DETAILED DISCUSSION OF THE INVENTION

Figure 9:
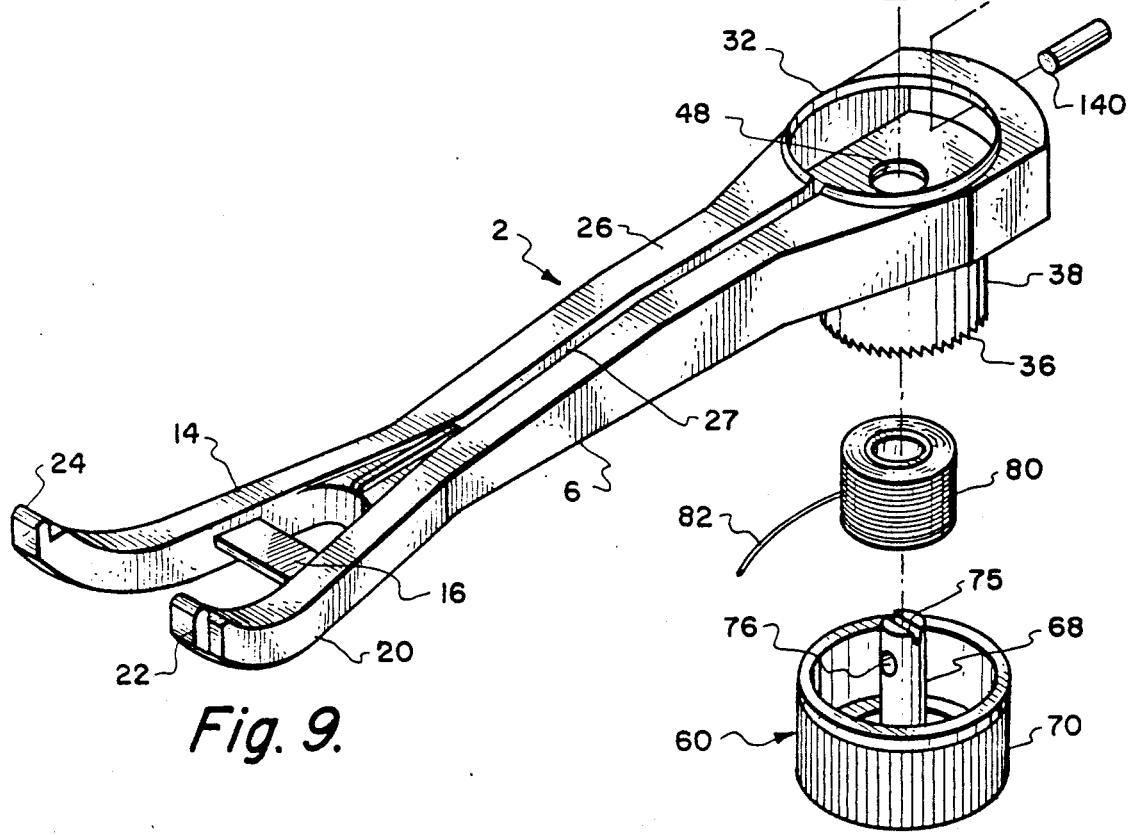
FIG. 9 is an exploded view of the frame, the locking pin, the take-up reel, the spring washer, the spool of dental floss, and the feed knob.
Figure 10:
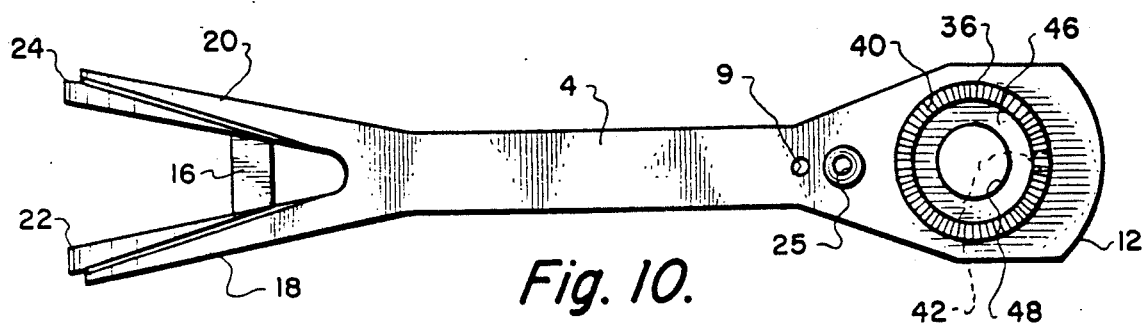
FIG. 10 is a top plan view of the frame of the dental floss holder invention.

Reference will now be made to the Figures. In FIG. 9 the six components, or pieces, which comprise the invention are illustrated in an exploded view. The six pieces are: the frame 2; the feed knob 60; the spool 80 of new unused dental floss 82; the take-up reel 110; the spring washer 120; and the locking pin 140.

The largest component which is the frame 2, has a top 4, a bottom 6, a mid-section 8, a front 10, and a back 12. There is a forked arm means positioned towards the front of the frame for holding and tensing a portion 84 of dental floss. The forked arm means is illustrated as a Y-shaped fork 14 having a cross-brace 16 between the two forks 18 and 20 for strength. The Y-shaped fork also has guides 22 and 24 for guiding and aligning the dental floss generally labeled 82.

A handle means is formed at the mid-section of the frame for allowing the user of the invention to grasp and manipulate the flosser while the user is flossing his/her teeth. The handle means is illustrated as a constricted neck portion 26 in the drawings. There is a longitudinal open gap 27 running along the bottom of the frame and extending between the forked arm 14 and the housing compartment 28.

There is a housing means towards the back of the frame for housing a spool 80 of unused dental floss and also for storing the used dental floss 100. The housing means is illustrated as an enlarged end 28 with an upright open crown projection 30 on the top 4 of the frame, a relatively large circular opening 32 in the bottom 6 of the frame 2 and a rear opening 33. The upright crown projection 30 is further described as an upright cylindrically-shaped hollow crown projection 30 having a bottom rim 34, a top rim 36, a side wall 38, and extending above the top of the frame for housing a spool 80 of new and unused dental floss. The top rim 36 of the crown has a circular array of inclined serrated teeth 40. The side wall 38 has a small hole or eyelet 42 located towards the back 12 of the frame 2 for allowing the end of the dental floss 82 to be threaded and passed through, wrapped partially around the outside of the crown projection 30 and out and beyond the crown projection. The bottom rim 34 of the crown projection 30 is permanently secured to the top 4 of the frame 2 and forms a bottom cavity 46 with the side wall 38. When the frame is made from a plastic material in an injection mold, the crown projection is integrally formed as a projection 30 extending from the frame 2. The area where the bottom rim joins the top of the frame has the appearance of a circular recess 46. Within this recess is a concentric circular opening 48 in the top of the frame 2, which is much smaller in diameter than the bottom circular rim 34 of the crown projection 30.

As previously stated, the upright cylindrically-shaped hollow crown projection 30 has a bottom rim 34, a top rim 36, a side wall 38, and the projection extends upwardly from the top surface area of the frame 2. The crown projection is used to house the spool 80 of unused dental floss 82. The side wall 38 of the cylindrically-shaped crown projection has a small hole 42 for allowing the end of the unused dental floss to pass through. The small hole opens towards the back of the frame. The bottom rim 34 of the crown projection is permanently secured to and is integral with the top of the frame. The top rim of the crown projection has a circular array of inclined serrated teeth 40. The cavity 46 or base formed at the bottom rim area of the crown projection has a circular opening or hole 48 which is concentric with but much smaller than the bottom rim of the crown projection.

Figure 15B:
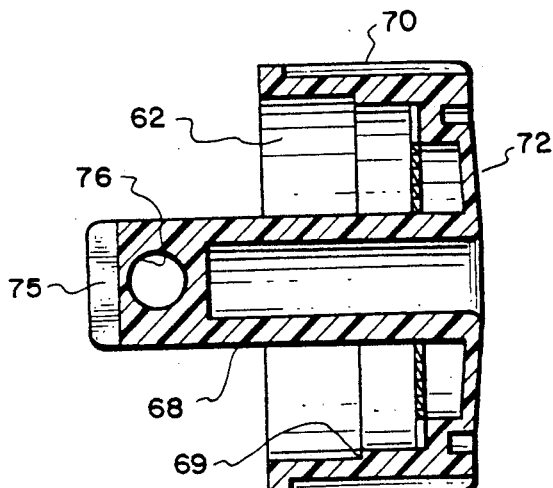
Figure 15A:
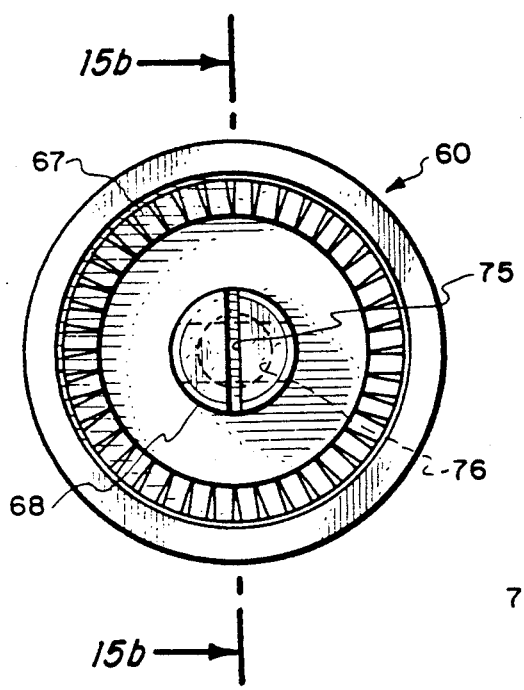
FIG. 15a bottom plan view of the feed knob.
Figure 15C:
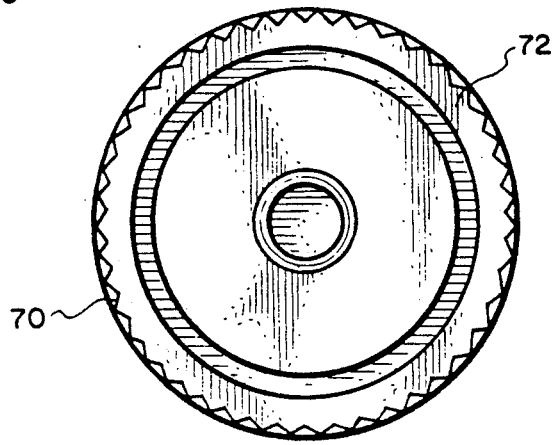
FIG. 15c is a top plan view of the feed knob.

The feed knob 60 illustrated in FIG. 9, is also illustrated in a bottom plan view in FIG. 15a, a top plan view in FIG. 15b and in cross section in FIG. 15b will now be described in further detail. The feed knob is described as having an upright, hollow, cylindrical shape. The knob has a circular open bottom 62 and which is for closely fitting over the cylindrically shaped hollow crown projection 30. The feed knob has a top rim 64, a bottom rim 66, an inside wall 69 and an outside wall 70. The feed knob includes a circular cap 72 integral with the top rim 64 of the feed knob 60. The cap 72 has an outside face and an inside face. There is a circular array of serrated teeth 67 around the circumference of the inside face of the cap. This array of circular teeth is for complementary engagement with the array of inclined serrated teeth 40 on the top rim of the cylindrically-shaped crown projection 30. There is a hollowed out axial spindle 68 which has one end permanently secured to the inside face of the cap 72 of the feed knob 60. The other end 74 of the axial spindle is unattached and extends beyond and below the lower rim 66 of the feed knob 60. The unattached end 74 of the spindle has a diametrical bore 76 transversely positioned inboard from the bottom of the spindle. There is also a transverse diametral groove 75 cut in the bottom tip of the spindle.

Figure 1:
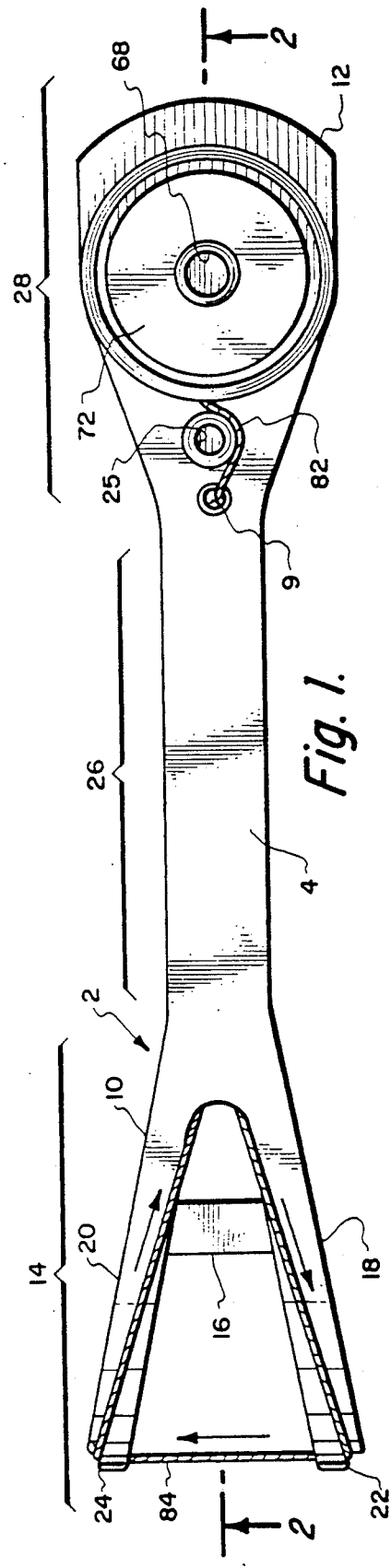
FIG. 1 is a top plan view of the dental floss holder invention.
Figure 2:
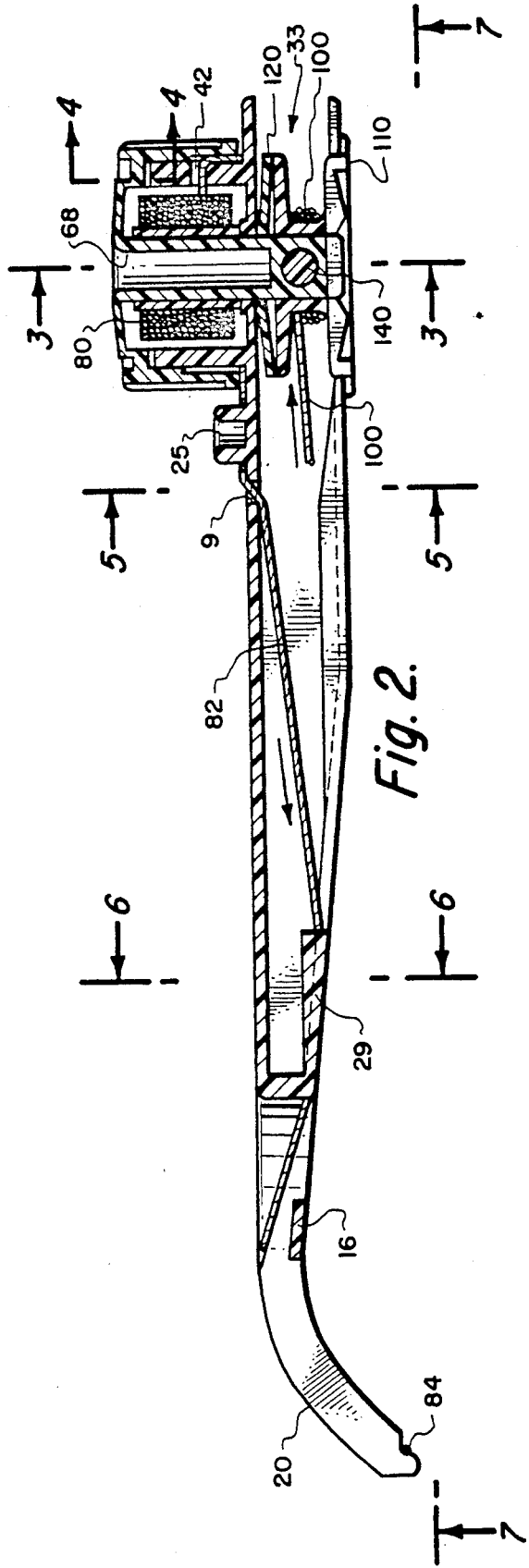
FIG. 2 is a longitudinal sectional elevational view taken along the line 2—2 of FIG. 1.
Figure 8:
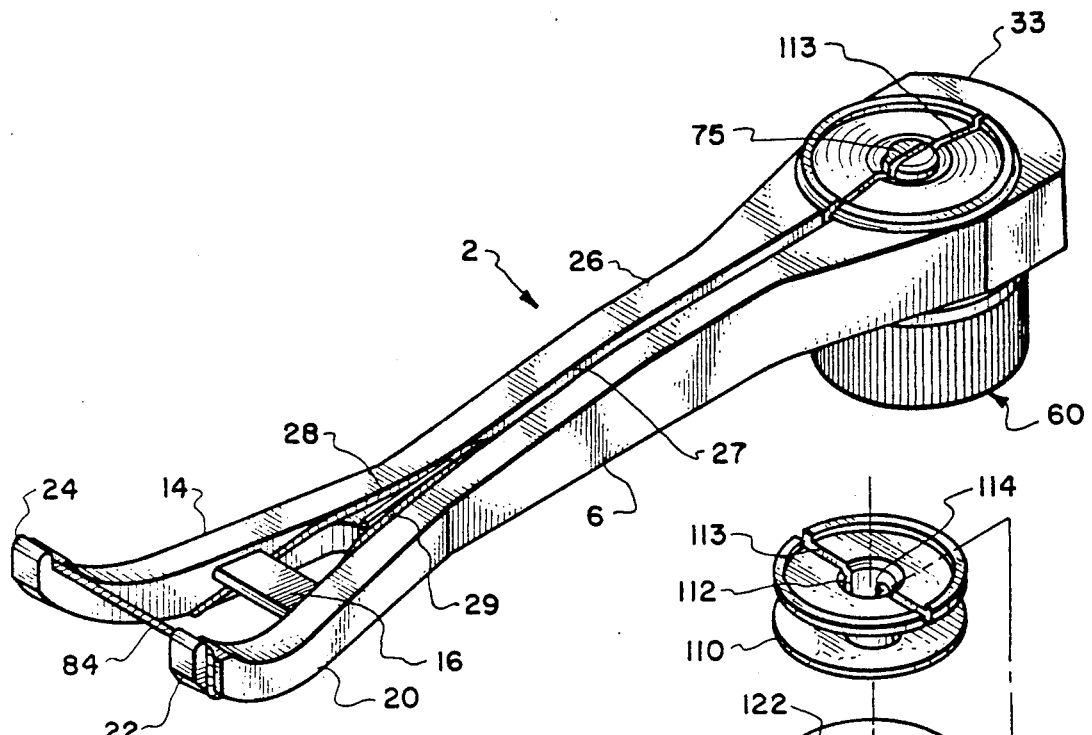
FIG. 8 is a bottom perspective view of the assembled dental flosser invention with the dental floss strung in place.
Figure 11:
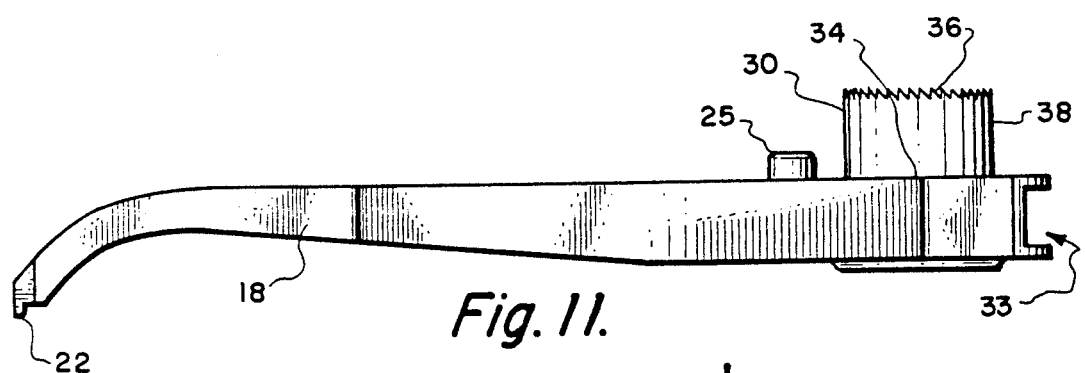
FIG. 11 is side elevational view of the frame.
Figure 12A:
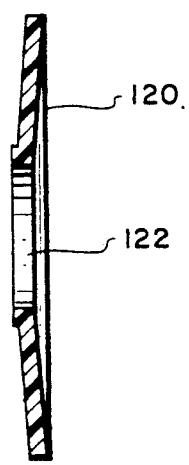
FIG. 12a is a sectional view of the spring washer taken along the line 12a—12a of FIG. 12b.
Figure 12B:
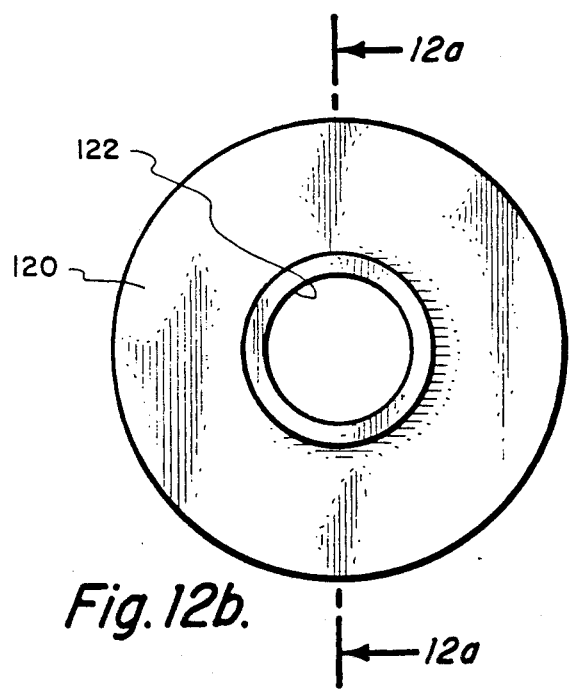
FIG. 12b is a top plan view of the spring washer.
Figure 13A:
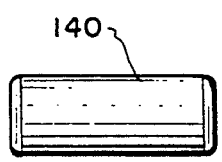
FIG. 13a is a side elevational view of the locking pin.
Figure 13B:
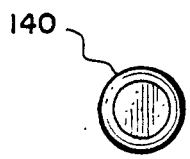
FIG. 13b is an end elevational view of the locking pin.
Figure 14A:
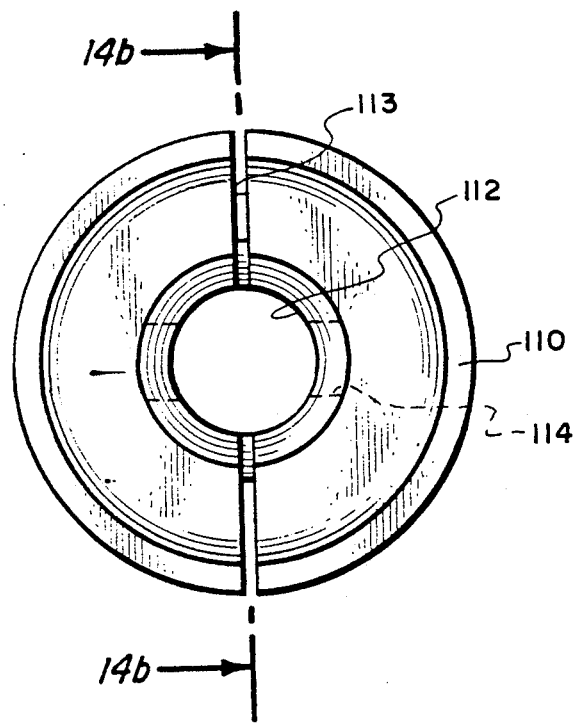
FIG. 14a is bottom plan view of the take-up reel.
Figure 14B:
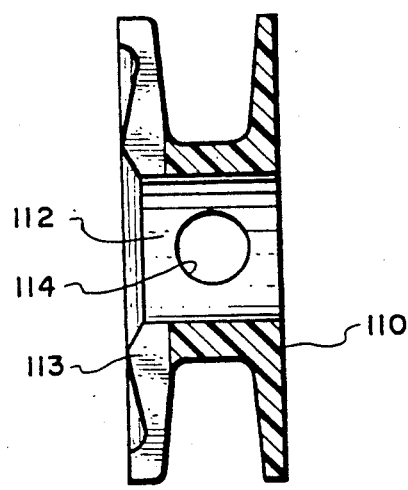

The rear portion of the frame 2 as illustrated in FIGS. 2 and 11 will now be described in greater detail. The frame 2 has a relatively large circular opening 32 in the bottom of and towards the back 12 of the frame 2. It is concentric with the circular opening 48 in the top of the frame which is concentric with the crown projection 30. This large, circular opening 32 is the opening for a cavity for storing the used floss 100 in the frame 2.

There is a take-up reel 110 positioned in the housing where the relatively large circular opening is, and this take-up reel is used for taking up and storing the used floss 100 as it is used. Also positioned inside of this circular opening and housing is a spring biasing means for mounting onto the feed knob spindle 68. The spring 120 is placed inside of the housing and its purpose is to tense the bottom lip 66 of the feed knob 60 against the top surface 4 of the frame 2. The spring biasing means is illustrated as a belleville washer 120. The belleville washer 120 is circular in configuration with a concentric hole 122. It looks like a typical conventional washer except that the top and bottom surfaces are both slightly cone shaped in the same direction so that the washer is not completely flat. When pressure is forced against either surface of the washer, it tends to flex a little bit thereby creating a spring or bias pushing against the part that is pressing against either face of the washer.

When the four components are assembled together, that is, when the belleville washer 120 is placed on the feed knob spindle 68 and the take-up reel 110 is placed adjacent to the feed knob 60, the locking pin 140 positioned at the bottom of the spindle will keep the take-up reel secured to the end of the spindle. This securement and also the limited length of the spindle 68 results in a limited space available for the belleville spring washer 120 to be positioned inside of the housing on the spindle and pushing against the underside face of the frame. This continuing tensioning by the spring washer forces the bottom of the feed knob rim 66 to press down against the outside of the frame in the circumferential area around the outside of the crown projection 30. This pressing down forces the portion of dental floss extending through the hole in the crown projection to be crimped on the top 4 of the frame.

There is a spool 80 of unused floss 82 placed in the hollow area of the cylindrically-shaped crown projection 30. The loose end of the floss is threaded through the small hole 42 in the wall of the crown projection 30. The floss is then threaded around the guide post 25 of the frame and through another hole 9 in the top of the frame and across the tips 22 and 24 of the forked arm 14 and then it is threaded back to the housing at the back of the frame and then secured to the take-up reel 110. In a preferred embodiment, there is a guide post 25 positioned adjacent to the feed knob 60 and in front of the feed knob on the top 4 of the frame 2. Located adjacent to the guide post 25 is a an eyelet 9 opening to allow the loose end of the floss 82 to be threaded through the eyelet 9, and it traverses along the interior of the frame 2 until it is exposed again towards the forked arm 14. The purpose of the guide post 25 also is to assist in the tensing of the dental floss 82 in order to keep it sufficiently taut while in use, and to provide a means for the user to increase the floss tension by threading the floss with a complete turn around the guide post 25. The crimping action and friction on the floss exiting under the feed knob lip 66 and around the guide post 25 are sufficient to prevent the floss from easily unwinding from the spool 80 caused by tension being placed against the strung dental floss while in use. The feed knob 60 is positioned over the crown projection 30 and the spindle 68 extends into the housing through the concentric opening 48 at the base of the crown projection. This opening 48 forms a tight fit around the spindle 68 to isolate the unused, fresh new floss 82 from the spent floss 100. The unattached end of the feed knob spindle passes initially through the concentric bore 112 of the take-up reel. This takes place during the assembly steps. As previously stated, the take-up reel 110 is attached towards the end of the spindle 68. The feed knob 60, the spool of fresh floss 82, the spring washer 120 and the take-up reel 110 are all positioned in that same sequence and they are concentrically positioned along the spindle 68 of the feed knob 60. After the take-up reel 110 is secured to the end of the spindle 68 and everything is properly assembled, then the feed knob spindle 68 and take-up reel 110 are all rotatable as a unit whenever the feed knob 60 is turned. The take-up reel 110 has a transverse diametrical bore 114, and the end of the feed knob spindle likewise has a transverse diametrical bore 76. These two bores 114 and 76 are lined up so that a locking pin 140 of the same dimensions and length as the combined bores is positioned into the bores to secure the take-up reel 110 to the end of the spindle 68.

The bottom of the take-up reel, which is exposed at the bottom of the frame 2, has a diametral slit 113 and the bottom of the spindle 68 likewise has a diametral groove 75. The two are cut such that when the take-up reel 110 is mounted on the spindle 68 by means of the locking pin 140, the groove 75 on the spindle and the slit 113 on the take-up reel 110 are aligned.

After the flosser is assembled, the interaction of the array of the inclined serrated teeth 40 on the crown projection 30 and the array of inclined serrated teeth 67 on the inside face of the cap 72 of the feed knob 60, along with the tensing action resulting by the spring washer 120 all form a clutch mechanism such that the feed knob 60 and the attached take-up reel 110 can rotate in only one direction in one-step increments.

The feed knob and crown projection have a clutch mechanism allowing the feed knob and take-up reel to rotate in only one direction and to frictionally engage and hold the floss at the spool end and to temporarily disengage the floss when the feed knob is rotated to allow a measured amount of fresh floss to unwind from the freely rotatable spool, while simultaneously reeling in a like amount of spent floss onto the take-up reel. The clutch mechanism rotates in incremental steps to advance new floss across the forked arm. The clutch mechanism also prevents the take-up reel from unwinding when the feed knob is at its at-rest position. Additional guide posts and guideways 28 and 29 on the frame also provide tautness to the strung dental floss to keep it sufficiently taut while the invention is being used to floss teeth.

The clutch mechanism formed by the complementary array of circular teeth 40 on the crown projection and the inside cap of the feed knob and the spring loaded washer is intended to provide a means to traverse the floss along its track in a controlled fashion to allow new floss to be unwound from the dental flosser while the used floss is being taken up concurrently by the take-up reel and yet to prevent any slack from occurring along the track of the dental floss. The inclined array of complementary teeth allows the feed knob to rotate in one direction only; in this case clockwise. As the pair of inclined teeth rise up on each other in response to torque being placed on the feed knob by the user, the rotation will proceed increment by increment resulting in a "clicking" noise. During this clicking operation, the feed knob moves axially away from the body of the frame a small amount due to the mating inclined teeth 40 and 67 rising up on each other. Thus the pressure on the floss under the lip 66 of the feed knob is reduced and it is when the teeth jump over each other that the basic floss tension is established. When the manual rotation of the feed knob stops, the ratchet teeth 40 and 67 completely mesh and full pressure returns under the feed knob lip 66 so that the floss supply side is locked. The ratchet teeth completely mesh and full pressure returns under the feed knob lip so that the floss supply side is locked. The ratchet teeth do not allow the take-up reel to unwind. As a result, the basic tension of the exposed floss is maintained during flossing. Each incremental feed knob rotation results in a small portion of the floss being moved one increment along the floss track of the invention.

To restring the cut floss, one merely has to align the slit 113 on the reel along with the bottom slit 27 previously formed in the bottom of the frame. One can thread the loose end of the floss through the slit on the reel and out through the open end 33 of the housing area of the frame. While holding the loose end, one rotates the feed knob 60 sufficiently so that a portion of the floss string 82 winds on to the take up reel to secure it to the take-up reel 110 and thereby maintaining the tension on the floss as it was before.

While the present invention has been shown and described herein in what is conceived to be the best mode contemplated, it is recognized that departures may be made therefrom within the scope of the invention which is therefore not to be limited to the details disclosed herein, but is to be afforded the full scope of the invention.

What is claimed is:

1. A disposable dental floss holder and flosser comprising:
    a frame having a top, a bottom, a midsection, a front, and a back;
    forked arm means positioned towards said front of said frame for holding and tensing a portion of dental floss;
    guide means on said frame for guiding a section of dental floss;
    handle means formed at said midsection of said frame for allowing the user to manipulate the flosser while flossing the user's teeth;
    housing means towards said back of said frame for housing a spool of unused dental floss, and storing used dental floss;
    said housing means includes an upright cylindrically-shaped hollow crown projection having a bottom rim, a top rim, a side wall, and extending above said top of said frame for housing said spool of unused dental floss;
    said side wall of said cylindrically-shaped crown projection having a small hole for allowing said dental floss from said unused spool to pass through;
    said bottom rim of said cylindrically-shaped hollow crown projection being permanently secured to and integral with said top of said frame;
    said top rim of said cylindrically-shaped hollow crown projection having a circular array of inclined serrated teeth;
    a circular opening in said top of said frame concentric with and much smaller than said bottom rim of said cylindrically shaped crown projection;
    an upright hollow cylindrically-shaped feed knob having a circular open bottom and for closely fitting over said cylindrically-shaped hollow crown projection, and having a top rim, a bottom rim, an inside wall, and an outside wall:
    said feed knob includes a circular cap integral with said top rim of said feed knob and having an outside face and an inside face;
    a circular array of serrated teeth around the circumference of said inside face of said cap on said feed knob for complementary engagement with said array of inclined serrated teeth on said top rim of said cylindrical crown projection;
    an axial spindle having one end permanently secured to said inside face of said cap and having its other unattached end extending beyond and below said feed knob;
    said unattached end of said spindle having a diametral bore transversely positioned inboard from said bottom of said spindle;
    a relatively large circular opening in said bottom of, and towards said back of said frame and concentric with said circular opening in said top of said frame and concentric with said crown projection, for allowing a means for storing the used floss to be positioned in said housing of said frame;
    reel means positioned in said housing where said relatively large circular opening is for taking up and storing the used floss as it is being used;
    spring biasing means for mounting on said feed knob spindle and inside said housing for biasing the bottom lip of said feed knob against said top surface of said frame;
    said spool of unused floss placed in the hollow of said cylindrically-shaped crown projection, said loose end of said floss threaded through said small hole in said wall of said crown projection, threaded along said guide means including said forked arm and threaded back to said housing at said back of said frame and attached to said reel means;
    said feed knob being positioned over said crown projection with said spindle extending into said housing through said concentric opening at said base of said crown projection, said opening and said spindle having a tight fit to isolate said unused floss from the spent floss;
    said unattached end of said spindle of said feed knob being inserted in said concentric bore of said take up spool;

means for securing said take-up reel to said end of said spindle;

said spool of floss, said spring washer means, and said take-up reel means all being in that sequence and concentrically positioned along said spindle of said feed knob;

said feed knob, spindle, and take-up spool being rotatable as a unit whenever said feed knob is turned;

the interaction of said array of inclined serrated teeth on said crown projection and said array of inclined serrated teeth on said inside face of said cap of said feed knob and said tensing action of said spring washer forming a clutch mechanism such that said feed knob and attached take-up spool can rotate in only one direction in one step increments.

2. The dental flosser invention as recited in claim 1 wherein said means for securing said take-up reel to said end of said spindle includes:

a locking pin inserted in said mutually aligned diametral bore of said axial shaft and said diametral bore of said take-up reel for securing said take-up reel to said shaft of said feed knob and preventing rotation of said take-up reel independently of said feed knob so that said take-up reel and said feed knob rotate as a unit.

3. The dental flosser invention as recited in claim 1 including a means for reattaching a broken end of dental floss which comprises:

a diametral slit on said take-up reel and a diametral slit on said axial shaft of said take-up reel, both of which are in alignment as a result of said locking pin and said bore on said axial shaft;

said broken end of said unused dental floss being restrung across said forked arm, passed through the bottom slit of said frame, through said diametral slit on said take-up reel and through said housing end of said frame and holding said broken end while rotating said feed knob for reeling onto and resecuring said end of said floss to said take-up reel.

4. The dental flosser invention as recited in claim 1 including a means for increasing the tension of the floss strung across said forked area.

5. The dental floss invention as recited in claim 4 wherein said means for increasing the tension of the floss includes a guide post for looping the unused floss around it after the floss exits between said bottom lip of said feed knob and said top of said frame.

* * * * *